(12) United States Patent
Levy et al.

(10) Patent No.: US 9,109,255 B2
(45) Date of Patent: Aug. 18, 2015

(54) METHODS AND COMPOSITIONS FOR DETERMINING RESPONSIVENESS TO ANTIBODY THERAPY

(75) Inventors: Ronald Levy, Stanford, CA (US); Wen-Kai Weng, Saratoga, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1594 days.

(21) Appl. No.: 11/155,308

(22) Filed: Jun. 16, 2005

(65) Prior Publication Data

US 2006/0008825 A1 Jan. 12, 2006

Related U.S. Application Data

(60) Provisional application No. 60/580,986, filed on Jun. 18, 2004.

(51) Int. Cl.
*C12Q 1/68* (2006.01)
*C12P 19/34* (2006.01)
*A61K 39/395* (2006.01)

(52) U.S. Cl.
CPC ........ *C12Q 1/6886* (2013.01); *C12Q 2600/106* (2013.01); *C12Q 2600/118* (2013.01); *C12Q 2600/172* (2013.01)

(58) Field of Classification Search
CPC ........... A61K 39/39558; C12Q 1/6827; C12Q 1/6886; C07K 16/2887; C07K 2317/732; G01N 2333/70535; G01N 2800/52; G01N 33/57407
See application file for complete search history.

(56) References Cited

U.S. PATENT DOCUMENTS

| | | | |
|---|---|---|---|
| 5,736,137 | A | 4/1998 | Anderson et al. |
| 5,985,561 | A | 11/1999 | Kimberly et al. |
| 2003/0219818 | A1 | 11/2003 | Bohen et al. |
| 2005/0064417 | A1 | 3/2005 | Watier et al. |

OTHER PUBLICATIONS

Goldsby et al Immunology, Fifth Edition, section "Cross-Reactivity," p. 141.*
DePalma A. 'Capturing Proteins Using Antibody Arrays' from Genomic and Proteomics (2005), available from www.adeplama.com., pp. 1-5.*
Weng W.K. et al 'Genetic polymorphism of the inhibitory IgG Fc receptor Fc gamma RIIb is not associated withclinical outcome of rituximab treated follicular lymphoma patients.' Blood, (Nov. 16, 2005) vol. 106, No. 11, Part 1, pp. 683A. Abstract provided pp. 1-2.*
Carlotti E. et al 'FcgammaRIIIA and FcgammaRIIA polymorphisms do not predict clinical outcome of follicular non-Hodgkin's lymphoma patients treated with sequential CHOP and rituximab.' Haematologica. Aug. 2007;92(8):1127-30.*
Witzig T.E. et al 'Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma.' J Clin Oncol. May 15, 2002;20(10):2453-63.*
Galimberti S. et al 'The efficacy of rituximab plus Hyper-CVAD regimen in mantle cell lymphoma is independent of FCgammaRIIIa and FCgammaRIIa polymorphisms.' J Chemother. Jun. 2007;19(3):315-21.*
Weng, W.-K. et al 'Immunoglobulin G Fc receptor polymorphisms and clinical course in follicular lymphoma patients.' Blood, (Nov. 16, 2004) vol. 104, No. 11, Part 1, pp. 887A, Abstract provided, p. 1.*
Juppner H. 'Functional properties of the PTH/PTHrP receptor.' Bone. Aug. 1995;17(2 Suppl):39S-42S.*
Hacker U.T. et al 'Lack of association between an interleukin-1 receptor antagonist gene polymorphism and ulcerative colitis.' Gut. May 1997;40(5):623-7.*
Zhang W. et al. 'FCGR2A and FCGR3A polymorphisms associated with clinical outcome of epidermal growth factor receptor expressing metastatic colorectal cancer patients treated with single-agent cetuximab.' J Clin Oncol. Aug. 20, 2007;25(24):3712-8.*
Musolino A. et al 'Immunoglobulin G fragment C receptor polymorphisms and clinical efficacy of trastuzumab-based therapy in patients with HER-2/neu-positive metastatic breast cancer.' J Clin Oncol. Apr. 10, 2008;26(11):1789-96.*
Cheung N.-K. V. et al. FCGR2A polymorphism is correlated with clinical outcome after immunotherapy of neuroblastoma with anti-GD2 antibody and granulocyte macrophage colony-stimulating factor. J Clin Oncol. Jun. 20, 2006;24(18):2885-90.*
Kim D.H. et al. Blood (Oct. 15, 2006) vol. 108, No. 8, pp. 2720-2725.*
Fabisiewicz A. et al. EJC Supplements (Sep. 2007), vol. 5, No. 4, p. 359 Abstract Only.*
Mitrovic Z. et al. Haematologica (2007) vol. 97, pp. 998-999.*
Thisted R.A. "What is a P-value?" (May 25, 1998) printed from www.stat.uchicago.edu/~thisted, pp. 1-6.*
Louis et al. "Association Between Polymorphism in IgG Fc Receptor IIIa Coding Gehe and Biological Response to Infliximab in Crohn's Disease," Aliment Pharmacol Ther. (2004) 19:511-519.

(Continued)

*Primary Examiner* — Stephen Kapushoc
(74) *Attorney, Agent, or Firm* — Bret E. Field; Bozicevic, Field & Francis LLP

(57) ABSTRACT

Methods and compositions are provided for determining whether a subject suffering from a neoplastic condition is responsive to an antineoplastic therapy, such as antibody therapy, e.g., Rituximab. In practicing the subject methods, the subject is genotyped to determine whether the subject has a least one favorable FcγR polymorphism, e.g., the 131 H/H genotype or the 158 V/V genotype. In addition, reagents, devices and kits thereof, that find use in practicing the subject methods are provided.

12 Claims, 11 Drawing Sheets

(56) References Cited

OTHER PUBLICATIONS

Farag et al. "FcγrIIIa and FcγRIIa Polymorphisms Do Not Predict Response to Rituximab in B-Cell Chronic Lymphocytic Leukemia," Blood (2004) 103(4):1472-1474.

Weng at al. "Two Immunoglobulin G Fc Receptor Polymorphisms Independently Predict Response to Rituximab in Patients with Follicular Lymphoma," Journal of Clinical Oncology (2003) 21(21)1-8.

Cartron at al. "Therapeutic Activity of Humanized Anti-CD20 Monoclonal Antibody and Polymorphism in IgG Fc Receptor FcγRIIIa Gene," Blood (2002) 99(3):754-758.

Dall'Ozzo et al. "Rituximab-Dependent Cytotoxicity by Natural Killer Cells: Influence of FCGR3A Polymorphism on the Concentration—Effect Relationship," Cancer Research (2004) 64:4664-4669.

Arepally et al. "FcγRIIA H/R [131] Polymorphism, Subclass-Specific IgG Anti-Heparin/Platelet Factor 4 Antibodies and Clinical Course in Patients with Heparin-Induced Thrombocytopenia and Thrombosis," Blood (1997) 89:370-375.

Canfield et al. "The Binding Affinity of Human IgG for its High Affinity Fc Receptor is Determined by Multiple Amino Acids in the $C_H2$ Domain and is Modulated by the Hinge Region," J. Exp. Med. (1991) 173:1483-1491.

Koene et al. "FcγRIIIa-158V/F Polymorphism Influences the Binding of IgG by Natural Killer Cell FcγRIIIa, Independently of the FcγRIIIa-48L/R/H Phenotype," Blood (1997) 90(3):1109-1114.

Sanders et al. "Human immunoglobulin G (IgG) Fc Receptor IIa (CD32) Polymorphism and IgG2-Mediated Bacterial Phagocytosis by Neutrophils," Infection and Immunitiy (1995) 63(1):73-81.

Shields et al. "High Resolution Mapping of the Binding Site on Human IgG1 for FcγRI, FcγRII, FcγRIII, and FcRn and Design of IgG1 Variants with Improved Binding to the FcγR," The Journal of Biological Chemistry (2001) 276(9):6591-6604.

Wines et al. "The IgG Fc Contains Distinct Fc Receptor (FcR) Binding Sites: The Leukocyte Receptors FcγRI and FcγRIIa Bind to a Region in the Fc Distinct from that Recognized by Neomatal FcR and Protein A," The Journal of Immunology (2000) pp. 5313-5318.

\* cited by examiner

Fig. 5

TABLE 1. CHARACTERISTICS OF THE PATIENTS ACCORDING TO
THEIR RESPONSE TO RITUXIMAB TREATMENT

| CHARACTERISTICS | NON RESPONSE (N=15) | PARTIAL RESPONSE (N=16) | COMPLETE RESPONSE (N=12) | ALL PATIENTS (N=43) |
|---|---|---|---|---|
| Sex (M/F) | 11/4 | 9/7 | 7/5 | 27/16 |
| Age (yr) | 49 ±8.8[#] | 56 ±14.9 | 52 ±7.5 | 52 ±11.5 |
| Pathology | | | | |
|   FSC* | 10 | 6 | 6 | 22 |
|   FM | 5 | 8 | 5 | 18 |
|   FLC | 0 | 2 | 1 | 3 |
| Number of Prior Chemotherapy | 1 - 3[‡] (2.0) | 0 - 6 (2.0) | 0 - 5 (1.0) | 0 - 6 (2.0) |
| Prior Transplant Therapy | 2 | 3 | 2 | 7 |
| Bulky Disease | 10 | 5 | 5 | 20 |
| Stage  III | 2 | 4 | 4 | 10 |
|        IV | 13 | 12 | 8 | 33 |
| ≥ 2 Extranodal | 3 | 3 | 2 | 8 |
| Time between Diagnosis and Treatment (Mo) | 56 ±35 | 69 ±40 | 65 ±42 | 63 ±38 |
| Estimated Tumor Cells[†] in Biopsied Samples (%) | 76 - 98[‡] (95) | 70 - 98 (92) | 72 - 98 (80) | |

\* FSC, follicular small cleaved
  FM, follicular mixed
  FLC, follicular large cell
[#] Plus-minus values are means ±SD
[‡] Range, values in parentheses are medians
[†] Calculation described in Method

Fig. 6

TABLE 2. CHARACTERISTICS OF THE PATIENTS ACCORDING TO THEIR Fcγ RECEPTOR POLYMORPHISM

| CHARACTERISTICS | FcγR IIIa Polymorphism | | | ALL PATIENTS (N=87) | FcγR IIa Polymorphism | | |
|---|---|---|---|---|---|---|---|
| | V/V (N=13) | V/F (N=40) | F/F (N=34) | | H/H (N=20) | H/R (N=43) | R/R (N=24) |
| Sex (M/F) | 9/4 | 23/17 | 16/18 | 48/39 | 10/10 | 27/16 | 11/13 |
| Age (yr) | 56 ±14.5[#] | 52 ±13.0 | 49 ±9.1 | 51 ±12.0 | 50 ±10.4 | 53 ±12.4 | 49 ±12.1 |
| Pathology | | | | | | | |
|   FSC* | 9 | 20 | 18 | 47 | 10 | 23 | 14 |
|   FM | 2 | 18 | 15 | 35 | 8 | 17 | 10 |
|   FLC | 2 | 2 | 1 | 5 | 2 | 3 | 0 |
| Number of Prior Chemotherapy | 0 - 5[‡] (1.0) | 0 - 4 (1.0) | 0 - 6 (1.0) | 0 - 6 (1.0) | 0 - 5 (1.0) | 0 - 6 (1.0) | 0 - 6 (1.0) |
| Prior Transplant Therapy | 1 | 4 | 5 | 10 | 1 | 8 | 1 |
| Bulky Disease | 6 | 22 | 18 | 46 | 9 | 21 | 15 |
| Stage  III | 1 | 9 | 6 | 16 | 5 | 9 | 2 |
|        IV | 12 | 31 | 28 | 61 | 15 | 34 | 22 |
| ≥ 2 Extranodal | 3 | 7 | 2 | 12 | 5 | 6 | 1 |
| Time between Diagnosis & Treatment (Mo) | 57 ±34 | 68 ±51 | 55 ±38 | 61 ±44 | 70 ±41 | 54 ±47 | 67 ±40 |

* FSC, follicular small cleaved
  FM, follicular mixed
  FLC, follicular large cell
[#] Plus-minus values are means ±SD
[‡] Range, values in parentheses are medians

Fig. 7

TABLE 3. CLINICAL RESPONSE TO RITUXIMAB THERAPY ACCORDING TO
THEIR Fcγ RECEPTOR IIIa POLYMORPHISM

|  | V/V | V/F | F/F | F Carrier[#] | $p$[‡] |
|---|---|---|---|---|---|
| 1-3 Months | | | | | |
| Objective Response* | 12/13 (92%) | 21/40 (53%) | 23/34 (68%) | 44/74 (59%) | *0.027* |
| 6 Months | | | | | |
| Objective Response | 11/13 (85%) | 15/38 (39%) | 15/29 (52%) | 30/67 (45%) | *0.013* |
| 9 Months | | | | | |
| Objective Response | 9/12 (75%) | 12/36 (33%) | 11/28 (39%) | 23/64 (36%) | *0.023* |
| 12 Months | | | | | |
| Objective Response | 9/12 (75%) | 8/35 (23%) | 8/27 (30%) | 16/62 (26%) | *0.002* |

\* Objective Response includes PR, partial response and CR/CRu, complete response/complete response unconfirmed
[#] F Carrier, combination of V/F and F/F genotypes
[‡] All *P* values are two-sided Fisher's exact test, comparing V/V to F Carrier

Fig. 8

TABLE 4. CLINICAL RESPONSE TO RITUXIMAB THERAPY ACCORDING TO THEIR FCγ RECEPTOR IIa POLYMORPHISM

|  | H/H | H/R | R/R | R Carrier[#] | $p^{\ddagger}$ |
|---|---|---|---|---|---|
| 1-3 Months | | | | | |
| Objective Response* | 16/20 (80%) | 27/43 (63%) | 13/24 (54%) | 40/67 (60%) | *0.116* |
| 6 Months | | | | | |
| Objective Response | 16/20 (80%) | 19/42 (45%) | 7/19 (37%) | 26/61 (43%) | *0.005* |
| 9 Months | | | | | |
| Objective Response | 14/20 (70%) | 13/39 (33%) | 5/17 (29%) | 18/56 (32%) | *0.004* |
| 12 Months | | | | | |
| Objective Response | 11/20 (55%) | 10/37 (27%) | 4/17 (24%) | 14/54 (26%) | *0.027* |

\* Objective Response includes PR, partial response and CR/CRu, complete response/complete response unconfirmed
[#] R Carrier, combination of H/R and R/R genotypes
[‡] All *P* values are two-sided Fisher's exact test, comparing H/H to R Carrier

Fig. 9

TABLE 5. ANALYSIS OF Fcγ RECEPTOR IIa
AND Fcγ RECEPTOR IIIa POLYMORPHISM

| FcγR IIa | FcγR IIIa | | |
|---|---|---|---|
| | V/V | F Carrier | (V/F, F/F) |
| H/H (N=20) | 3 (15%) | 17 (85%) | (14,3) |
| H/R (N=43) | V/V | F Carrier | (V/F, F/F) |
| | 8 (19%) | 35 (81%) | (16, 19) |
| R/R (N=24) | V/V | F Carrier | (V/F, F/F) |
| | 2 (8%) | 22 (92%) | (10,12) |

Fig. 10

TABLE 6. CLINICAL RESPONSE TO RITUXIMAB THERAPY ACCORDING TO
THEIR FCγ RECEPTOR IIa AND IIIa POLYMORPHISM

| 1-3 Months | Both 158 V/V and 131 H/H (N=3) | Either 158 V/V or 131 H/H (N=27) | Others (N=57) | $p^{\ddagger}$ |
|---|---|---|---|---|
| Objective Response* | 3/3 (100%) | 22/27 (81%) | 31/57 (54%) | *0.009* |
| 6 Months | | | | |
| Objective Response | 3/3 (100%) | 21/27 (78%) | 17/50 (34%) | *0.0001* |
| 9 Months | | | | |
| Objective Response | 3/3 (100%) | 17/26 (65%) | 12/47 (26%) | *0.0003* |
| 12 Months | | | | |
| Objective Response | 3/3 (100%) | 14/26 (54%) | 8/45 (18%) | *0.0004* |

\* Objective Response includes PR, partial response and CR/CRu, complete response/complete response unconfirmed
‡ All *P* values are two-sided Fisher's exact test, comparing 158 V/V and/or 131 H/H to Others

Fig. 11

TABLE 7. PROGNOSTIC FACTORS FOR CLINICAL RESPONSE: LOGISTIC REGRESSION ANALYSIS

|  | 1-3 Month | 6 Month | 9 Month | 12 Month |
|---|---|---|---|---|
| 158 V/V | 12.25 *<br>(1.35-111.16)<br>*0.026* [#] | 8.48<br>(1.54-46.60)<br>*0.014* | 7.94<br>(1.59-39.76)<br>*0.012* | 17.14<br>(2.94-100.18)<br>*0.002* |
| 131 H/H | 2.96<br>(0.85-10.35)<br>*0.090* | 8.03<br>(2.13-30.21)<br>*0.002* | 6.26<br>(1.86-21.06)<br>*0.003* | 7.25<br>(1.89-27.84)<br>*0.004* |
| Stage III vs IV | 0.66<br>(0.19-2.22)<br>*0.498* | 1.01<br>(0.28-3.62)<br>*0.984* | 0.62<br>(0.16-2.40)<br>*0.486* | 0.78<br>(0.16-3.85)<br>*0.759* |
| Age ≥ 60 | 3.08<br>(0.57-16.76)<br>*0.193* | 2.62<br>(0.57-12.12)<br>*0.217* | 1.73<br>(0.35-8.53)<br>*0.500* | 4.22<br>(0.73-24.25)<br>*0.107* |
| Prior Transplant Therapy | 0.86<br>(0.30-2.43)<br>*0.772* | 0.55<br>(0.17-1.73)<br>*0.304* | 1.24<br>(0.39-3.95)<br>*0.717* | 2.18<br>(0.56-8.45)<br>*0.261* |
| Bulky Disease | 1.81<br>(0.54-6.05)<br>*0.336* | 0.62<br>(0.17-2.27)<br>*0.470* | 0.68<br>(0.18-2.53)<br>*0.563* | 0.47<br>(0.11-2.14)<br>*0.333* |
| ≥ 2 Extranodal | 1.22<br>(0.30-4.89)<br>*0.784* | 0.32<br>(0.06-1.69)<br>*0.181* | 0.57<br>(0.11-2.84)<br>*0.489* | 0.23<br>(0.03-1.87)<br>*0.170* |

\* Odds ratio: relative odds of response to rituximab treatment, values in parentheses are 95% confidence intervals

[#] All $P$ values are two-sided and considered to be statistically significant for $P<0.05$

METHODS AND COMPOSITIONS FOR DETERMINING RESPONSIVENESS TO ANTIBODY THERAPY

CROSS-REFERENCE TO RELATED APPLICATIONS

Pursuant to 35 U.S.C. §119(e), this application claims priority to the filing date of the U.S. Provisional Patent Application Ser. No. 60/580,986 filed Jun. 18, 2004; the disclosure of which is herein incorporated by reference.

ACKNOWLEDGMENT OF GOVERNMENT SUPPORT

This invention was made with Government support under Grant Nos. CA 34233 and CA 33399 awarded by the National Institute of Health. The Government has certain rights in this invention.

INDRUDUCTION

1. Background of the Invention

In the fall of 1997, the anti-CD20 monoclonal antibody, rituximab (currently sold under the brand name RITUXAN®, was approved for the treatment of refractory or relapsed low-grade B-cell non-Hodgkin's lymphoma (NHL). Rituximab has since become a mainstay of treatment for low-grade NHL and over 400,000 patients worldwide have been treated with rituximab. Despite this extensive clinical experience, the mechanism of action of rituximab remains unclear, as does the nature of resistance.

Rituximab is a chimeric antibody consisting of a murine CD20-binding variable region linked to human IgG1 constant region. CD20 is a cell surface protein expressed on B-lymphocytes. CD20 has four transmembrane domains and has been proposed to act as an ion channel; however, the function of CD20 remains poorly understood.

Phase II trials of rituximab in people with refractory or relapsed low grade or follicular NHL demonstrated a 50% response rate. While the nature of de novo resistance to rituximab is unclear, such resistance is very rarely due to loss of the CD20 antigen, which cannot be shed or internalized and is rarely down-regulated. Despite these properties of CD20, acquired resistance to rituximab is common in that only half of patients previously responding to rituximab will respond to a second course of treatment.

An effective and practical diagnostic protocol which could provide information as to whether a patient is or is not responsive to rituximab would be desirable for a number of reasons, including avoidance of delays in alternative treatments, elimination of exposure to adverse effects of rituximab and reduction of unnecessary expense.

As such, there is interest in the development of a protocol that can accurately predict whether or not a patient is responsive to rituximab therapy.

2. Relevant Literature

Articles of interest include: Louis et al., Aliment Pharmacol Ther. 2004 March; 19(5):511-9.; Farag et al., Blood. 2004 Feb. 15; 103(4):14724; Weng & Levy, J Clin Oncol. 2003 Nov. 1; 21(21):3940-7; and Catron et al., Blood. 2002 Feb. 1; 99(3):754-8. Also of interest is published U.S. Patent Application 20030219818.

SUMMARY OF THE INVENTION

Methods and compositions are provided for determining whether a subject suffering from a neoplastic condition is responsive to an antineoplastic therapy, such as antibody therapy, e.g., Rituximab therapy. In practicing the subject methods, the subject is genotyped to determine whether the subject has a least one favorable FcγR polymorphism, e.g., the 131H/H genotype or the 158 VN genotype. In addition, reagents, devices and kits thereof, that find use in practicing the subject methods are provided.

BRIEF DESCRIPTION OF THE FIGURES

FIGS. 5, 6, 7, 8, 9, 10 and 11 provide Tables 1 to 7 referred to in the Experimental Section, below.

DESCRIPTION OF THE SPECIFIC EMBODIMENTS

Figure 1:
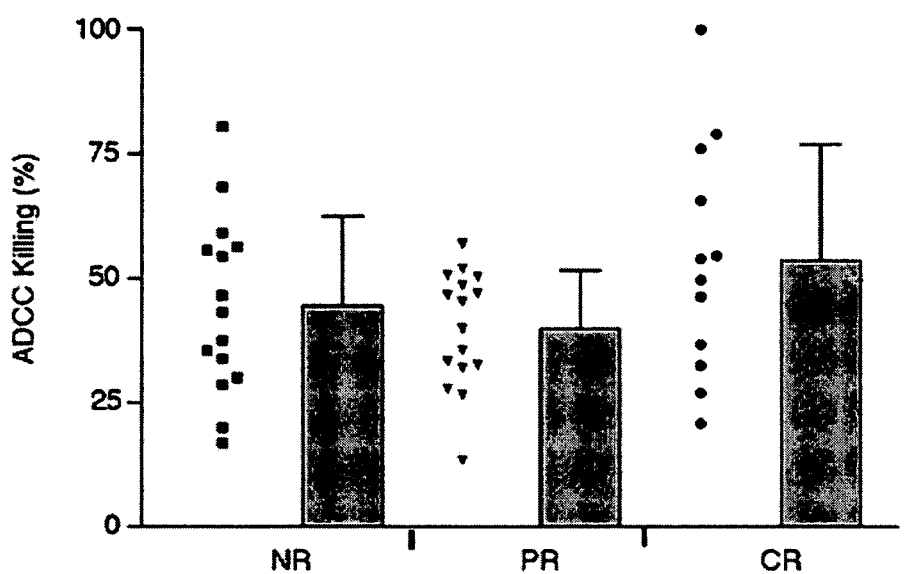
FIG. 1. Rituximab-induced antibody-dependent cellular cytotoxicity (ADCC). The scatter plot in the left column of each group represents the degree of rituximab-induced ADCC (effector/target ratio at 30:1) of individual tumors. The bars represent the mean and standard deviations in each group. NR, nonresponder; PR, partial responder; CR, complete responder or complete response unconfirmed.

Methods and compositions are provided for determining whether a subject suffering from a neoplastic condition is responsive to an antineoplastic therapy, such as antibody therapy, e.g., Rituximab therapy. In practicing the subject methods, the subject is genotyped to determine whether the subject has a least one favorable FcγR polymorphism, e.g., the 131H/H genotype or the 158 V/V genotype. In addition, reagents, devices and kits thereof that find use in practicing the subject methods are provided.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention is directed to methods of determining whether a subject suffering from a neoplastic condition is responsive to a particular therapy, such as antibody therapy, as well as reagents and kits thereof (and devices) for use in practicing the subject methods. In further describing the invention, the subject methods are described first, followed by a review of the reagents, kits and devices for use in practicing the subject methods.

Methods of Determining Whether a Subject Suffering from a Neoplastic Condition is Responsive to a Particular Therapy The subject invention provides methods of determining whether a patient or subject suffering from a neoplastic disease, i.e., hyperproliferative disorder, is responsive to a particular therapy, such as antibody therapy. Hyperproliferative disorders, or malignancies, are conditions in which there is unregulated cell growth. The methods of the present invention are directed at hyperproliferative disorders and particularly whether such a disorder will or will not be responsive to a particular antineoplastic therapy, e.g., antibody therapy. The disorder may be characterized by the presence or absence of solid tumors.

In certain embodiments, the subject methods are directed to determining whether a B-cell hyperproliferative disorder, e.g., NHL, is responsive to therapeutic antibody therapy. B-cell hyperproliferative disorders are those disorders that derive from cells in the B cell lineage, typically including hematopoietic progenitor cells expressing B lineage markers, pro-B cells, pre-B cells, B-cells and memory B cells; and that express markers typically found on such B lineage cells.

Of particular interest are non-Hodgkin's lymphomas (NHLs), which are a heterogeneous group of lymphoproliferative malignancies with different patterns of behavior and responses to treatment. Like Hodgkin's disease, NHL usually originates in lymphoid tissues and can spread to other organs, however, NHL is much less predictable than Hodgkin's disease regarding their responses to therapy and has a far greater predilection to disseminate to extranodal sites. The NHLs can be divided into 2 prognostic groups: the indolent lymphomas and the aggressive lymphomas. Indolent NHL types have a relatively good prognosis, with median survival as long as 10 years, but they usually are not curable in advanced clinical stages. The aggressive type of NHL has a shorter natural history. A number of these patients can be cured with intensive combination chemotherapy regimens, but there is a significant number of relapses, particularly in the first 2 years after therapy.

Among the NHL are a variety of B-cell neoplasms, including precursor B-lymphoblastic leukemia/lymphoma; peripheral B-cell neoplasms, e.g. B-cell chronic lymphocytic leukemia; prolymphocytic leukemia; small lymphocytic lymphoma; mantle cell lymphoma; follicle center cell lymphoma; marginal zone B-cell lymphoma; splenic marginal zone lymphoma; hairy cell leukemia; diffuse large B-cell lymphoma; T-cell rich B-cell lymphoma, Burkitt's lymphoma; high-grade B-cell lymphoma, (Burkitt-like); etc.

Follicular lymphoma comprises 70% of the indolent lymphomas reported in American and European clinical trials. Most patients with follicular lymphoma are over age 50 and present with widespread disease at diagnosis. Nodal involvement is most common, often accompanied by splenic and bone marrow disease. The vast majority of patients are diagnosed with advanced stage follicular lymphoma and are not cured with current therapeutic options, and the rate of relapse is fairly consistent over time, even in patients who have achieved complete responses to treatment. Subtypes include follicular small cleaved cell (grade 1) and follicular mixed small cleaved and large cell (grade 2). Another subtype of interest is follicular large cell (grade 3 or FLC) lymphoma which can be divided into grades 3a and 3b.

Marginal zone lymphomas were previously included among the diffuse small lymphocytic lymphomas. When marginal zone lymphomas involve the nodes, they are called monocytoid B-cell lymphomas, and when they involve extranodal sites (gastrointestinal tract, thyroid, lung, breast, skin), they are called mucosa-associated lymphatic tissue (MALT) lymphomas. Many patients have a history of autoimmune disease, such as Hashimoto's thyroiditis or Sjogren's syndrome, or of Helicobacter gastritis. Most patients present with stage I or II extranodal disease, which is most often in the stomach. When disseminated to lymph nodes, bone marrow, or blood, this entity behaves like other low-grade lymphomas. Large B-cell lymphomas of MALT sites are classified and treated as diffuse large cell lymphomas.

Splenic marginal zone lymphoma is an indolent lymphoma that is marked by massive splenomegaly and peripheral blood and bone marrow involvement, usually without adenopathy. This type of lymphoma is otherwise known as splenic lymphoma with villous lymphocytes, an uncommon variant of B-cell chronic lymphocytic leukemia. Management of this entity usually starts with splenectomy which is different than other low-grade lymphomas. If/when the disease progresses after splenectomy, it tends to be managed like other low grade lymphomas.

Among the aggressive forms of NHL is diffuse large B-cell lymphoma, which is the most common of the non-Hodgkin's lymphomas, comprising 30% of newly-diagnosed cases. Most patients present with rapidly enlarging masses, often with symptoms both locally and systemically. Relapses after treatment are not uncommon, depending on the presence of various risk factors. Lymphomatoid granulomatosis is an EBV positive large B-cell lymphoma with a predominant T-cell background. The histology shows association with angioinvasion and vasculitis, usually manifesting as pulmonary lesions or paranasal sinus involvement. Patients are managed like others with diffuse large cell lymphoma.

Primary mediastinal B-cell lymphoma is a subset of diffuse large cell lymphoma characterized by significant fibrosis on histology. Patients are usually female and young. Patients present with a locally invasive anterior mediastinal mass which may cause respiratory symptoms or superior vena cava syndrome. Therapy and prognosis are the same as for other comparably-staged patients with diffuse large cell lymphoma, except for advanced-stage patients with a pleural effusion, who have an extremely poor prognosis (progression-free survival is less than 20%) whether the effusion is cytologically positive or negative.

Mantle cell lymphoma is found in lymph nodes, the spleen, bone marrow, blood, and sometimes the gastrointestinal system (lymphomatous polyposis). Mantle cell lymphoma is characterized by CD5-positive mantle zone B cells, a translocation of chromosomes 11 and 14, and an overexpression of the cyclin D1 protein. The median survival is significantly shorter (3-5 years) than that of other lymphomas, and this histology is now considered to be an aggressive lymphoma. A diffuse pattern and the blastoid variant have an even more aggressive course with shorter survival, while the mantle zone type may have a more indolent course. Refractoriness to chemotherapy is a usual feature.

Lymphoblastic lymphoma is a very aggressive form of NHL. It often occurs in young patients, but not exclusively. It is commonly associated with large mediastinal masses and has a high predilection for disseminating to bone marrow and the central nervous system (CNS). Treatment is usually patterned after that for acute lymphoblastic leukemia (ALL). Since these forms of NHL tend to progress so quickly, combination chemotherapy is instituted rapidly once the diagnosis has been confirmed. Careful review of the pathologic specimens, bone marrow aspirate and biopsy specimen, cerebrospinal fluid cytology, and lymphocyte marker constitute the most important aspects of the pretreatment staging workup.

Burkitt's lymphoma/diffuse small noncleaved cell lymphoma typically involves younger patients and represents the most common type of pediatric non-Hodgkin's lymphoma. These aggressive extranodal B-cell lymphomas are characterized by translocation and deregulation of the c-myc gene on chromosome 8. A subgroup of patients with dual translocation of c-myc and bcl-2 appear to have an extremely poor outcome despite aggressive therapy. Treatment of Burkitt's lymphoma/diffuse small noncleaved cell lymphoma involves aggressive multidrug regimens similar to those used for the advanced-stage aggressive lymphomas.

Patients who undergo transplantation of the heart, lung, liver, kidney, or pancreas usually require life-long immunosuppression. Life-long immunosuppression may result in post-transplantation lymphoproliferative disorder (PTLD), which appears as an aggressive lymphoma. Pathologists can distinguish a polyclonal B-cell hyperplasia from a monoclonal B-cell lymphoma; both are almost always associated with EBV. In some cases, usually for the polyclonal forms of the disease, withdrawal of immunosuppression results in eradication of the lymphoma. When this is unsuccessful or not feasible, a combination chemotherapy is usually used. EBV-negative post-transplantation lymphoproliferative disorders occur late and have a particularly poor prognosis. Chronic lymphocytic leukemia (CLL) is a disorder of morphologically mature but immunologically less mature lymphocytes and is manifested by progressive accumulation of these cells in the blood, bone marrow, and lymphatic tissues. Lymphocyte counts in the blood are usually equal to or higher than 10,000 per cubic millimeter. At present there is no curative therapy. CLL occurs primarily in middle-aged and elderly individuals, with increasing frequency in successive decades of life. The clinical course of this disease progresses from an indolent lymphocytosis without other evident disease to one of generalized lymphatic enlargement with concomitant pancytopenia. Complications of pancytopenia, including hemorrhage and infection, represent a major cause of death in these patients. Immunological aberrations, including Coombs-positive hemolytic anemia, immune thrombocytopenia, and depressed immunoglobulin levels may all complicate the management of CLL. CLL lymphocytes coexpress the B-cell antigens CD19 and CD20 along with the T-cell antigen CD5. CLL B cells express relatively low levels of surface-membrane immunoglobulin (compared with normal peripheral blood B cells). CLL is diagnosed by an absolute increase in lymphocytosis and/or bone marrow infiltration coupled with the characteristic features of morphology and immunophenotype.

AIDS-related lymphomas are comprised of a narrow spectrum of histologic types consisting almost exclusively of B-cell tumors of aggressive type. These include diffuse large cell lymphoma; B-immunoblastic; and small non-cleaved, either Burkitt's or Burkift's like. The HIV-associated lymphomas can be categorized into: primary central nervous system lymphoma (PCNSL); systemic lymphoma; and primary effusion lymphoma. All of these lymphomas differ from non-HIV-related lymphomas in their molecular characteristics, presumed mechanism of pathogenesis, treatment, and clinical outcome. All 3 pathologic types are equally distributed and represent aggressive disease. In general, the clinical setting and response to treatment of patients with AIDS-related lymphoma is very different from the non-HIV patients with lymphoma. The HIV-infected individual with aggressive lymphoma usually presents with advanced-stage disease that is frequently extranodal. The clinical course is more aggressive, and the disease is both more extensive and less responsive to chemotherapy. Immunodeficiency and cytopenias, common in these patients at the time of initial presentation, are exacerbated by the administration of chemotherapy. Therefore, treatment of the malignancy increases the risk of opportunistic infections that, in turn, further compromise the delivery of adequate treatment.

Acute lymphocytic leukemia (ALL) generally has an aggressive course, depending in part on the presence of the Philadelphia (Ph) chromosome. Patients with Ph chromosome-positive ALL are rarely cured with chemotherapy. Many patients who have molecular evidence of the bcr-abl fusion gene, which characterizes the Ph chromosome, have no evidence of the abnormal chromosome by cytogenetics.

Although the methods of the invention are primarily applied to NHL, in some cases treatment may be used in cases of Hodgkin's lymphoma, which is a lymphoma characterized by a pleomorphic lymphocytic infiltrate with malignant multinucleated giant cells. Most cases of Hodgkin's disease probably arise from germinal center B cells that are unable to synthesize immunoglobulin. The majority of cases in developing countries and about one third of those in the United States are associated with the presence of Epstein-Barr virus in the Reed-Sternberg cells. Treatment strategies depend on a number of factors including the presence of B symptoms, the histologic subtype, gender, and sexual maturity. To date there are several published studies demonstrating the effectiveness of Rituxan for CD20-positive Hodgkin's disease, particularly the lymphocyte predominant variant.

Other neoplastic disease conditions whose responsiveness to antibody therapy can be evaluated according to the subject methods include, but are not limited to: colorectal cancer, non-small cell lung cancer, small cell lung cancer, ovarian cancer, breast cancer, head and neck cancer, renal cell carcinoma, and the like.

As summarized above, the subject methods may be used to evaluate the responsiveness of a subject to a given antineoplastic therapy. Antineoplastic therapies of interest include, but are not limited to: chemotherapy, radiation therapy, antibody therapy, etc.

By therapeutic antibody therapy is meant a treatment protocol or regimen that includes administration of a therapeutic antibody agent. Representative therapeutic antibody agents specifically bind to antigens present on B cells, particularly hyperproliferative B cells, e.g. B lineage lymphomas and leukemias, and the like. The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. Fragments comprise a portion of a full-length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. In some aspects of the invention, a combination of one or more antibodies with different specificities, either for epitopes of a single antigen, or for multiple antigens, may be used.

Markers that are specifically found on B cells include CD45R, which is an exon specific epitope found on essentially all B cells, and is maintained throughout B cell development (Coffman et al., (1982) Immunol. Rev. 69:5-23). The B cell markers CD19, CD20; CD22; CD23 are selectively expressed on B cells and have been associated with B cell malignancies (Kalil and Cheson (2000) Drugs Aging 16(1): 9-27; U.S. Pat. No. 6,183,744, herein incorporated by reference). Surface immunoglobulin, including epitopes present on the constant regions or idiotypic determinants, is a specific marker for B cells and has been utilized in immunotherapy (Caspar et al. (1997) Blood 90(9):3699-706). The MB-1 antigen is found on all normal immunoglobulin (Ig)-expressing cells, but not on T cells, thymocytes, granulocytes, or platelets, and expressed by virtually all Ig-expressing B cell tumors (Link et al. (1986) J Immunol 137(9):3013-8). Other B cell antigens of interest known to be expressed, for example, on non-Hodgkin's lymphomas, are Muc-1; B5; BB1; and T9 (Freedman et al. (1987) Leukemia 1(1):9-15).

Of particular interest is the CD20 antigen, also known as "Bp35". (Note that CD20 was called B1 early in the course of research on B-cell markers). CD20 is a human B cell marker that is expressed during early pre-B cell development and remains until plasma cell differentiation. The CD20 molecule may regulate a step in the activation process that is required for cell cycle initiation and differentiation, and is usually expressed at very high levels on neoplastic B cells. Thus, the CD20 surface antigen can be targeted for treating B cell lymphomas. U.S. Pat. No. 5,736,137, herein incorporated by reference, describes the chimeric antibody "C2B8" that binds the CD20 antigen and its use to treat B cell lymphoma (antibody is also known as Rituxan®, rituximab, Mabthera (this is a trademark in Europe)).

In a preferred embodiment, the antibody is a monoclonal antibody. Monoclonal antibodies are highly specific, being directed against a single antigenic site, and each monoclonal antibody is directed against a single determinant on the antigen. For example, the monoclonal antibodies to be used in accordance with the present invention may be made by the hybridoma method first described by Kohler et al. (1975) Nature 256:495, or may be made by recombinant DNA methods (see, e.g., U.S. Pat. No. 4,816,567). The monoclonal antibodies may also be isolated from phage antibody libraries using the techniques described in Clackson et al., (1991) Nature 352:624-628 (1991) and Marks et al. (1991) J. Mol. Biol. 222:581-597 (1991), for example. For clinical use, the monoclonal antibodies may be humanized forms of non-human antibodies. These are chimeric antibodies that contain sequences derived from both human and non-human immunoglobulin. For the most part, humanized antibodies are human immunoglobulins in which residues from a hypervariable region of the recipient are replaced by residues from a hypervariable region of a non-human species having the desired specificity, affinity, and capacity.

Specificity, as used herein, refers to the affinity of the antibody, and to the cross-reactivity with other antigens. In order to consider an antibody interaction to be "specific", the affinity will be at least about $10^{-7}$ M, usually about $10^{-8\ to\ -9}$ M, and may be up to $10^{-11}$ or higher for the epitope of interest. It will be understood by those of skill in the art that the term "specificity" refers to such a high affinity binding, and is not intended to mean that the antibody cannot bind to other molecules as well. One may find cross-reactivity with different epitopes, due, e.g. to a relatedness of antigen sequence or structure, or to the structure of the antibody binding pocket itself. Antibodies demonstrating such cross-reactivity are still considered specific for the purposes of the present invention.

In practicing the subject methods, a subject or patient sample, e.g., cells or collections thereof, e.g., tissues, is assayed to determine whether the host or subject from which the assayed sample was obtained is responsive to a given therapy, e.g., therapeutic antibody therapy. In practicing the subject diagnostic methods, the sample obtained from the host is assayed to determine the genotype of the host or subject from which the sample was obtained with respect to at least one, i.e., one or more, polymorphisms, where polymorphisms of interest are referred to herein as target polymorphisms. In certain embodiments, the at least one target polymorphism is a FcγR polymorphism. A FcγR polymorphism is a polymorphism present in an FcγR (immunoglobulin fragment C receptor) protein. FcγR proteins of interest include, but are not limited to, FcγRII proteins (e.g., FcγRIIa, also known as CD32 (whose amino acid and nucleotide sequence is present at Genbank accession nos. NM_021642 or M28697)); FcγRIII proteins (e.g., FcγRIIIa, also known as CD16 (whose amino acid and nucleotide sequence is present at Genbank accessin nos. BC036723; BC033678; BC017865 and NM_000569)), and the like. In certain embodiments, the sample is assayed to determine the genotype of the host with respect to a single target polymorphism, where in these embodiments, the single target polymorphism is an FcγRII polymorphism, such as an FcγRIIa polymorphism, where a specific representative FcγRIIa polymorphism of interest is the FcγRIIa 131 H/R polymorphism (where the nucleotide codons encoding the H and R residues of the polymorphism are CAT and CGT, respectively). In certain embodiments, the sample is assayed to determine the genotype of the host with respect to two or more different target polymorphisms, where in these embodiments, the two or more different target polymorphisms include at least one FcγR polymorphism. In certain of these embodiments, at least two of the target polymorphisms are different FcγR polymorphisms, such as an FcγRII and an FcγRIII polymorphism. In certain embodiments, the sample is assayed for both an FcγRII polymorphism, such as the specific FcγRIIa polymorphisms described above, and an FcγRIII polymorphism, such as an FcγRIIIa polymorphism, inlcuding the FcγRIIa 158V/F polymorphism (where the nucleotide codons encoding the V and F residues of the polymorphism are GTT and TTT, respectively).

Any convenient protocol for assaying a sample for the above one or more target polymorphisms may be employed in the subject methods. In certain embodiments, the target polymorphism will be detected at the protein level, e.g., by assaying for a polymorphic protein. In yet other embodiments, the target polymorphism will be detected at the nucleic acid level, e.g., by assaying for the presence of nucleic acid polymorphism, e.g., an single nucleotide polymorphism (SNP) that cause expression of the polymorphic protein.

For example, polynucleotide samples derived from (e.g., obtained from) an individual may be employed. Any biological sample that comprises a polynucleotide from the individual is suitable for use in the methods of the invention. The biological sample may be processed so as to isolate the polynucleotide. Alternatively, whole cells or other biological samples may be used without isolation of the polynucleotides contained therein. Detection of a target polymorphism in a polynucleotide sample derived from an individual can be accomplished by any means known in the art, including, but not limited to, amplification of a sequence with specific primers; determination of the nucleotide sequence of the polynucleotide sample; hybridization analysis; single strand conformational polymorphism analysis; denaturing gradient gel electrophoresis; mismatch cleavage detection; and the like. Detection of a target polymorphism can also be accomplished by detecting an alteration in the level of a mRNA transcript of the gene; aberrant modification of the corresponding gene, e.g., an aberrant methylation pattern; the presence of a non-wild-type splicing pattern of the corresponding mRNA; an alteration in the level of the corresponding polypeptide; and/ or an alteration in corresponding polypeptide activity.

Detection of a target polymorphism by analyzing a polynucleotide sample can be conducted in a number of ways. A test nucleic acid sample can be amplified with primers which amplify a region known to comprise the target polymorphism (s). Genomic DNA or mRNA can be used directly. Alternatively, the region of interest can be cloned into a suitable vector and grown in sufficient quantity for analysis. The nucleic acid may be amplified by conventional techniques, such as a polymerase chain reaction (PCR), to provide sufficient amounts for analysis. The use of the polymerase chain reaction is described in a variety of publications, including, e.g., "PCR Protocols (Methods in Molecular Biology)" (2000) J. M. S. Bartlett and D. Stirling, eds, Humana Press; and "PCR Applications: Protocols for Functional Genomics" (1999) Innis, Gelfand, and Sninsky, eds., Academic Press. Once the region comprising a target polymorphism has been amplified, the target polymorphism can be detected in the PCR product by nucleotide sequencing, by SSCP analysis, or any other method known in the art. In performing SSCP analysis, the PCR product may be digested with a restriction endonuclease that recognizes a sequence within the PCR product generated by using as a template a reference sequence, but does not recognize a corresponding PCR product generated by using as a template a variant sequence by virtue of the fact that the variant sequence no longer contains a recognition site for the restriction endonuclease. PCR may also be used to determine whether a polymorphism is present by using a primer that is specific for the polymorphism. Such methods may comprise the steps of collecting from an individual a biological sample comprising the individual's genetic material as template, optionally isolating template nucleic acid (genomic DNA, mRNA, or both) from the biological sample, contacting the template nucleic acid sample with one or more primers that specifically hybridize with a target polymorphic nucleic acid molecule under conditions such that hybridization and amplification of the template nucleic acid molecules in the sample occurs, and detecting the presence, absence, and/or relative amount of an amplification product and comparing the length to a control sample. Observation of an amplification product of the expected size is an indication that the target polymorphism contained within the target polymorphic primer is present in the test nucleic acid sample. Parameters such as hybridization conditions, polymorphic primer length, and position of the polymorphism within the polymorphic primer may be chosen such that hybridization will not occur unless a polymorphism present in the primer(s) is also present in the sample nucleic acid. Those of ordinary skill in the art are well aware of how to select and vary such parameters. See, e.g., Saiki et al. (1986) *Nature* 324:163; and Saiki et al (1989) *Proc. Natl. Acad. Sci. USA* 86:6230. As one non-limiting example, a PCR primer comprising the T78C variation described in Example 1 may be used.

Alternatively, various methods are known in the art that utilize oligonucleotide ligation as a means of detecting polymorphisms. See, e.g., Riley et al. (1990) *Nucleic Acids Res.* 18:2887-2890; and Delahunty et al. (1996) *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid may be sequenced by a dideoxy chain termination method or other well-known methods. Genomic DNA or mRNA may be used directly. If mRNA is used, a cDNA copy may first be made. If desired, the sample nucleic acid can be amplified using a PCR. A variety of sequencing reactions known in the art can be used to directly sequence the relevant gene, or a portion thereof in which a specific polymorphism is known to occur, and detect polymorphisms by comparing the sequence of the sample nucleic acid with a reference polynucleotide that contains a target polymorphism. Any of a variety of automated sequencing procedures can be used. See, e.g., WO 94/16101; Cohen et al. (1996) *Adv. Chromatography* 36:127-162.

Hybridization with the variant sequence may also be used to determine the presence of a target polymorphism. Hybridization analysis can be carried out in a number of different ways. including, but not limited to Southern blots, Northern blots, dot blots, microarrays, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Identification of a polymorphism in a nucleic acid sample can be performed by hybridizing a sample and control nucleic acids to high density arrays containing hundreds or thousands of oligonucleotide probes. Cronin et al. (1996) *Human Mutation* 7:244-255; and Kozal et al. (1996) *Nature Med.* 2:753-759.

Single strand conformational polymorphism (SSCP) analysis; denaturing gradient gel electrophoresis (DGGE); mismatch cleavage detection; and heteroduplex analysis in gel matrices can also be used to detect polymorphisms. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels. The aforementioned techniques are well known in the art. Detailed description of these techniques can be found in a variety of publications, including, e.g., "Laboratory Methods for the Detection of Mutations and Polymorphisms in DNA" (1997) G. R. Taylor, ed., CRC Press, and references cited therein.

A number of methods are available for determining the expression level of a polymorphic nucleic acid molecule, e.g., a polymorphic mRNA, or polymorphic polypeptide in a particular sample. Diagnosis may be performed by a number of methods to determine the absence or presence or altered amounts of normal or abnormal mRNA in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc. The presence and/or the level of a polymorphic polypeptide may also be detected and/or quantitated in any Alternatively, one may focus on the expression of mRNA. Biochemical studies may be performed to determine whether a sequence polymorphism in a DGAT coding region or control regions is associated with disease. Disease associated polymorphisms may include deletion or truncation of the gene, mutations that alter expression level, that affect the activity of the protein, etc.

Screening for mutations in a polymorphic polypeptide may be based on the functional or antigenic characteristics of the protein. Protein truncation assays are useful in detecting deletions that may affect the biological activity of the protein. Various immunoassays designed to detect polymorphisms in polymorphic polypeptides may be used in screening. Where many diverse genetic mutations lead to a particular disease phenotype, functional protein assays have proven to be effective screening tools. The activity of the encoded a polymorphic polypeptide may be determined by comparison with a reference polypeptide lacking a specific polymorphism.

Diagnostic methods of the subject invention in which the level of polymorphic gene expression is of interest will typically involve comparison of the relevant nucleic acid abundance of a sample of interest with that of a control value to determine any relative differences, where the difference may be measured qualitatively and/or quantitatively, which differences are then related to the presence or absence of an abnormal gene expression pattern. A variety of different methods for determine the nucleic acid abundance in a sample are known to those of skill in the art, where particular methods of interest include those described in: Pietu et al., Genome Res. (June 1996) δ: 492-503; Zhao et al., Gene (Apr. 24, 1995) 156: 207-213; Soares, Curr. Opin. Biotechnol. (October 1997) δ: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Additional references describing various protocols for detecting the presence of a target polymorphism include, but are not limited to, those described in: U.S. Pat. Nos. 6,703,228; 6,692,909; 6,670,464; 6,660,476; 6,653,079; 6,632,606; 6,573,049; the dislcosures of which are herein incorporated by reference.

Following obtainment of the genotype from the sample being assayed, the genotype is evaluated to determine whether the subject/host/patient is responsive to the antineoplastic therapy of interest. In certain embodiments, the obtained genotype may be compared with a reference or control to make a diagnosis regarding the therapy responsive phenotype of the cell or tissue, and therefore host, from which the sample was obtained/derived. The terms "reference" and "control" as used herein mean a standardized genotype to be used to interpret the genotype of a given patient and assign a prognostic class thereto. The reference or control may be a genotype that is obtained from a cell/tissue known to have the desired phenotype, e.g., responsive phenotype, and therefore may be a positive reference or control genotype. In addition, the reference/control genotype may be from a cell/tissue known to not have the desired phenotype, and therefore be a negative reference/control genotype.

In certain embodiments, the obtained genotype is compared to a single reference/control genotype to obtain information regarding the phenotype of the cell/tissue being assayed. In yet other embodiments, the obtained genotype is compared to two or more different reference/control profiles to obtain more in depth information regarding the phenotype of the assayed cell/tissue. For example, the obtained genotype may be compared to a positive and negative genotype to obtain confirmed information regarding whether the cell/tissue has the phenotype of interest.

Representative examples of genotypes associated with therapy reponsiveness, particularly Rituximab responsive include, but are not limited to: the FcγRIIa 131H/H genotype and the FcγRIIa 158 V/V genotype. Representative examples of genotypes associated with therapy non-reponsiveness, particularly Rituximab-non responsiveness include, but are not limited to: the FcγRIIa 131H/R genotype; the FcγRIIa 131 R/R genotype; the FcγRIIa 158 V/F genotype; and the the FcγRIIIa 158 F/F genotype.

In many embodiments, the above-obtained information about the cell/tissue being assayed is employed to diagnose a host, subject or patient with respect to responsive to therapeutic antibody therapy, as described above. In certain embodiments, the above-obtained information is employed to give a refined probability determination as to whether a subject will or will not respond to a particular therapy. For example, an identification of the FcγRIIa 131H/H genotype and/or the FcγRIIa 158 V/V genotype may be employed to determine that the subject has at least a 70% chance, such as at least a 75% chance, including at least an 80% chance of responding to antibody, e.g., Rituximab, therapy. Likewise, an identification of the FcγRIIa 131H/R or R/R genotype and/or the FcγRIIIa 158 V/F or F/F genotype may be employed to determine that the subject has less than 50% chance, such as a less than 45% chance, including a less than 40% chance of responding to antibody, e.g., Rituximab, therapy.

The subject methods further find use in pharmacogenomic applications. In these applications, a subject/host/patient is first diagnosed for the presence of absence of a responsive phenotype using a protocol such as the diagnostic protocol described in the preceding section.

The subject is then treated using a pharmacological protocol, where the suitability of the protocol for a particular subject/patient is determined using the results of the diagnosis step. More specifically, where the identified phenotype is responsive, an appropriate therapeutic antibody treatment protocol is then employed to treat the patient. Alternatively, where a patient is identified as having a non-responsive phenotype, non-antibody protocols are then employed.

Reagents, Devices and Kits

Also provided are reagents, devices and kits thereof for practicing one or more of the above-described methods. The subject reagents, devices and kits thereof may vary greatly. Reagents and devices of interest include those mentioned above with respect to the methods of identifying the presence of the target polymorphisms, where such reagents may include nucleic acid primers, arrays of nucleic acid probes, antibodies to polymorphic polypeptides (e.g., immobilized on a substrate), signal producing system reagents, etc., depending on the particular detection protocol to be performed.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Materials and Methods
A. Patient Population

This study included 87 patients with follicular lymphoma, who were treated with rituximab at Stanford Medical Center between 1993 and 2003. They were selected because of the availability of their lymphoma tumor cells, peripheral blood or serum samples, and their known clinical response to rituximab. The pathology of all patient cases was reviewed. There were 47 patients with follicular small cleaved, 35 patients with follicular mixed, and five patients with follicular large-cell lymphoma. Fifteen patients had received rituximab as their first-line therapy. Seventy-two patients had received chemotherapy before rituximab, including 10 patients who had prior bone marrow transplantation. No patients received chemotherapy within the 2 months before rituximab treatment. Eighty-one patients had four weekly infusions of rituximab at 375 mg/m$^2$, five patients had eight weekly infusions of 375 mg/m$^2$, and one patient had four weekly infusions of 250 mg/m$^2$. Clinical responses were determined by physical examination and computed tomography scans between 1 and 3 months after last rituximab infusion and every 3 months thereafter. These responses were scored according to the Cheson criteria (Cheson B D, Horning S J, Coiffier B, et al: Report of an international workshop to standardize response criteria for non-Hodgkin's lymphoma. J Clin Oncol 17:1244-1253, 1999). Maximal clinical responses were observed at 1 to 3 months in all but three patients, who had partial responses at 1 to 3 months and showed additional tumor shrinkage at later time points. Pretreatment tumor cells were available in 43 patients and were used for in vitro ADCC assay. FcγR polymorphisms were analyzed in all 87 patients. This study was conducted according to a protocol approved by the institutional review board of our institution, and informed consent was obtained from all patients for the use of tissue samples and the analysis of clinical information.

B. Tumor Cells

Suspensions of pretreatment tumor cells isolated from lymph nodes were cryopreserved in liquid nitrogen. For ADCC assay, the tumor cells were thawed and subjected to Ficoll-Paque PLUS (Amersham Pharmacia Biotech, Piscataway, N.J.) gradient centrifugation to remove dead cells. The viability of tumor cells, determined by trypan blue dye exclusion at the time of assay, always exceeded 90%. The percentage of tumor cells in each sample was estimated by staining with antibodies specific for kappa or lambda light chains.

C. ADCC Assay

Lymphoma cells were labeled with chromium-51 ($^{51}$Cr) by incubating 3×10$^6$ cells with 450 μCi of $^{51}$Cr (Amersham Pharmacia Biotech) for 2 hours at 37° C. Cells were washed with RPMI-1640, and then incubated for 30 minutes at 37° C. with antibodies (at 10 μg/mL). Excess antibodies were removed by washing with medium. Mononuclear cells were obtained by Ficoll-Hypaque centrifugation of peripheral blood of a healthy donor (with FcγRIIIa 158 V/V genotype) and used as effector cells. One×10$^{4}$ $^{51}$Cr-labeled target cells were incubated for 4 hours at 37° C. with the indicated number of effector cells in 200 μL of RPMI-5 medium (RPMI-1640, 10 mmol/L HEPES, 5% heat-inactivated human AB serum, 1% $_L$-glutamine). Fifty microliters of medium was collected after 4 hours of incubation and counted in a Micro-Beta 1450 scintillation counter (Wallac, Turku, Finland). Spontaneous $^{51}$Cr release was determined in the absence of effector cells. Maximal $^{51}$Cr release was determined by lysis with 0.5% Triton X-100. All samples were assayed in triplicate. The specific $^{51}$Cr release was determined by subtracting the spontaneous $^{51}$Cr release from that of the treatment wells, then dividing the result by the maximal $^{51}$Cr release minus spontaneous $^{51}$Cr release. All the tumor samples had coexistent T cells of variable degree (Table 1). To compare different tumor samples, the specific ADCC is calculated by dividing the specific $^{51}$Cr release in rituximab-treated samples minus $^{51}$Cr release in control IgG1-treated samples by the percentage of CD20-positive cells in individual samples.

D. Analysis of FcRIIIa and FcRIIa Polymorphisms

Genomic DNA was prepared from tumor cells or from peripheral-blood mononuclear cells using a DNA extraction kit (Qiagen, Valencia, Calif.). In six patients, DNA was prepared from the serum using a described method.(Kopreski M S, Benko F A, Kwee C, et al: Detection of mutant K-ras DNA in plasma or serum of patients with colorectal cancer. Br J Cancer 76:1293-1299, 1997) Genotyping of FcγRIIIa 158 V/F and FcγRIIa 131 histidine (H)/arginine (R) polymorphism was performed by a polymerase chain reaction followed by allele-specific restriction enzyme digestion. (Koene H R, Kleijer M, Algra J, et al: Fc-gamma-RIIIa-158 V/F polymorphism influences the binding of IgG by natural killer cell Fc-gamma-RIIa, independently of the Fc-gamma-RIIIa48 UR/H phenotype. Blood 90:1109-1114, 1997; Jiang X-M, Arepally G, Poncz M, et al: Rapid detection of the Fc-gamma-RIIA-H/R 131 ligand-binding polymorphism using an allele-specific restriction enzyme digestion (ASRED). J Immunol Methods 199:55-59, 1996). All genotyping of FcγRIIIa polymorphism was confirmed by direct sequencing of the region of interest.

E. Statistical Analysis

Differences in the means of ADCC killing were tested by single-factor analysis of variance test and checked by the Kruskal-Wallis (nonparametric) test. The clinical responses of the patients were compared using a two-tailed Fisher's exact test (PRISM for Macintosh; GraphPad Software, San Diego, Calif.). A logistic regression analysis including age (or <60 years), stage (III v IV), presence of bulky disease, number of extranodal sites (two or <two), prior bone marrow transplantation, and FcRIIa and FcRIIIa genotype was used to identify independent prognostic variables influencing the clinical responses (StatView 5.0.1; SAS Inc, Cary, N.C.).

II. Results

A. Rituximab-Mediated ADCC in Follicular Lymphoma Cells

The ability of rituximab to mediate ADCC in follicular lymphoma cells was determined. Pretreatment lymphoma cells from 43 patients were tested using effector cells isolated from one healthy donor. Rituximab-mediated ADCC was detected in all 43 patient samples (range, 13.5% to 100%). As expected, the parental murine antibody of rituximab, 2B8, which contains a mouse γ1 Fc portion and binds lymphoma cells identically to rituximab, did not mediate ADCC (data not shown).

The relation of the observed ADCC susceptibility of lymphoma cells from individual patients to their clinical response to rituximab therapy was then evaluated. Patients were subdivdied into nonresponders (NR), partial responders (PR), and complete responders (CR) according to their response to rituximab at the first evaluation at 1 to 3 months (Table 1, FIG. 5). The range of ADCC varied widely in all three groups (NR, 16.9% to 80.6%; PR, 13.5% to 57.0%; CR, 20.9% to 100.0%; FIG. 1). However, there was no difference of rituximab-mediated ADCC between the three groups (means i standard deviations: NR, 44.6%±18%; PR, 40.0%±12%; CR, 53.6%±23%). Additional analysis showed no relationship between rituximab-mediated ADCC and response when clinical response was scored at 6, 9, or 12 months after treatment, nor did the susceptibility to ADCC correlate with the duration of remission (data not shown). In a subgroup of 29 patients whose tumors were studied in a report on complement-mediated cytotoxicity, (Weng W-K, Levy R: Expression of complement inhibitors CD46, CD55, and CD59 on tumor cells does not predict clinical outcome after rituximab treatment in follicular non-Hodgkin lymphoma. Blood 98:1352-1357, 2001) the expression of CD20 on their lymphoma cells had previously been determined by flow cytometric staining. Within this subgroup, there was no correlation between the expression of CD20 and rituximab-mediated ADCC ($r=-0.03$; $P=0.88$).

B. Clinical Response to Rituximab Therapy and FcγRIIa 158 V/F Polymorphism

The FcγRIIIa (CD16) of V allele demonstrates higher affinity to IgG1 than the F allele and mediates ADCC more effectively. Recently, Cartron et al (Cartron G, Dacheux L, Salles G, et al: Therapeutic activity of humanized anti-CD20 monoclonal antibody and polymorphism in IgG Fc receptor Fc-gamma-R IIIa gene. Blood 99:754-758, 2002) have shown an association between FcγRIIIa 158 V/V genotype and higher response rate in patients treated with first-line rituximab. This association was assayed in the subject patient group, the majority of whom were treated for relapsed disease. The study group was expanded to 87 by acquiring peripheral blood or serum samples from additional rituximab-treated patients.

Figure 2:
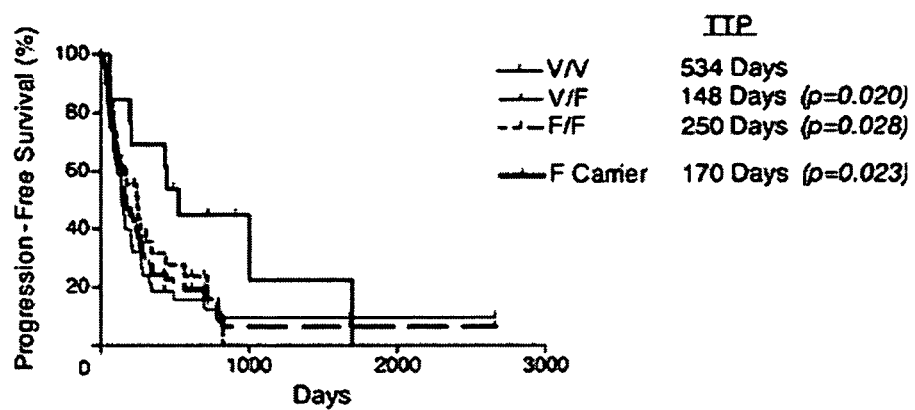
FIG. 2. Kaplan-Meier estimates of progression-free survival by immunoglobulin G fragment C receptor IIIa (FcγRIIa) 158 valine (V)/phenylalanine (F) polymorphism. Progression-free survival curves were plotted by FcγRIIIa 158 V/F genotype on all 87 patients. F carriers represent patients with either 158 V/F or 158 F/F genotype. TTP, median time to progression.

In this sample set, 13 patients (15%) had homozygous V/V (158 V/V), 40 (46%) had heterozygous V/F (158 V/F), and 34 (39%) had homozygous F/F (158 F/F). The three groups were not different in terms of average age at the time of treatment, number of prior chemotherapy courses, or time between diagnosis and treatment (Table 2, FIG. 6). The response rate in patients with 158 V/F and in patients with 158 F/F was similar at all four time points (Table 3, FIG. 7). For that reason, we grouped 158 V/F and 158 F/F together as the F carrier for statistical analysis. A significant difference was detected between the response rates of 158 V/V and F carriers (Table 3, FIG. 7). The progression-free survival (PFS) at 2 years was 45% for patients with 158 V/V, 12% for 158 V/F, 16% for 158 F/F, and 14% for F carriers, using the Kaplan-Meier estimation, with median time to progression (TTP) of 534, 148, 250, and 170 days for each group, respectively. The PFS estimate of patients with 158 V/V was significantly longer than that for patients with 158 V/F, 158 F/F, or F carriers (FIG. 2).

Figure 3:
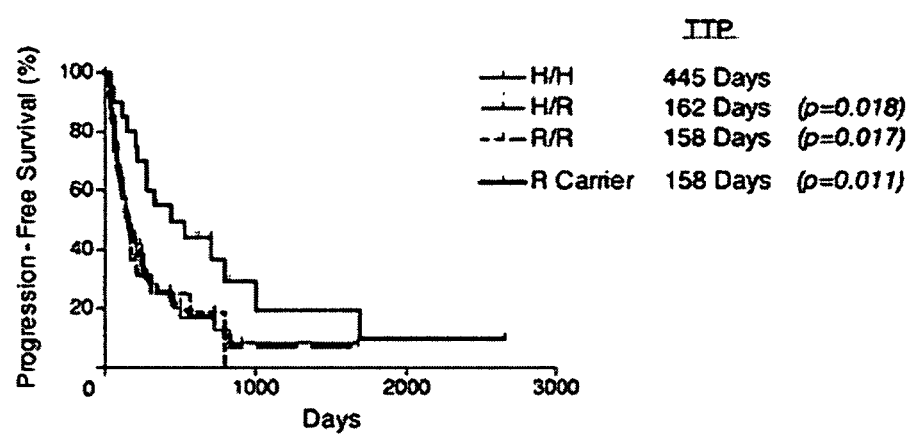
FIG. 3. Kaplan-Meier estimates of progression-free survival (PFS) by immunoglobulin G fragment C receptor IIa (FcγRIIa) 131 histidine (H)/arginine (R) polymorphism. PFS curves were plotted by FcγRIIa 131H/R genotype on all 87 patients. R carriers represent patients with either 131H/R or 131 R/R genotype. TTP, median time to progression.

C. Clinical Response to Rituximab Therapy and FcγRIIa 131H/R Polymorphism The FcγRIIa (CD32) is another activating FcγR that is expressed only on macrophages but not on natural killer (NK) cells. An H/R polymorphism at position 131 of FcγRIIa has been found to affect its affinity to human IgG(Jiang X-M, Arepally G, Poncz M, et al: Rapid detection of the Fc-gamma-RIIA-H/R131 ligand-binding polymorphism using an allele-specific restriction enzyme digestion (ASRED). J Immunol Methods 199:55-59, 1996). Of the 87 patients in the group, 20 (23%) had homozygous H/H (131H/H), 43 (49%) had heterozygous H/R (131H/R), and 24 (28%) had homozygous R/R (131 R/R). Once again, the three groups were not different in terms of average age at the time of treatment, number of prior chemotherapy treatments, or time between diagnosis and treatment (Table 2). Although there was no difference in the response rate at 1 to 3 months between the three groups, patients with 131H/H showed a significantly higher response rate than the other two groups combined (H/R and R/R [R carrier]) at 6, 9, and 12 months (Table 4, FIG. 8). This higher response rate also translated to longer remission: the PFS at 2 years was 37% for patients with 131H/H, 13% for 131H/R, 19% for 131 R/R, and 14% for R carrier using the Kaplan-Meier estimation with TTP of 445, 162, 158, and 158 days for each group, respectively. The PFS estimate for patients with 131H/H was significantly longer than for patients with other genotypes (FIG. 3.).

Figure 4:
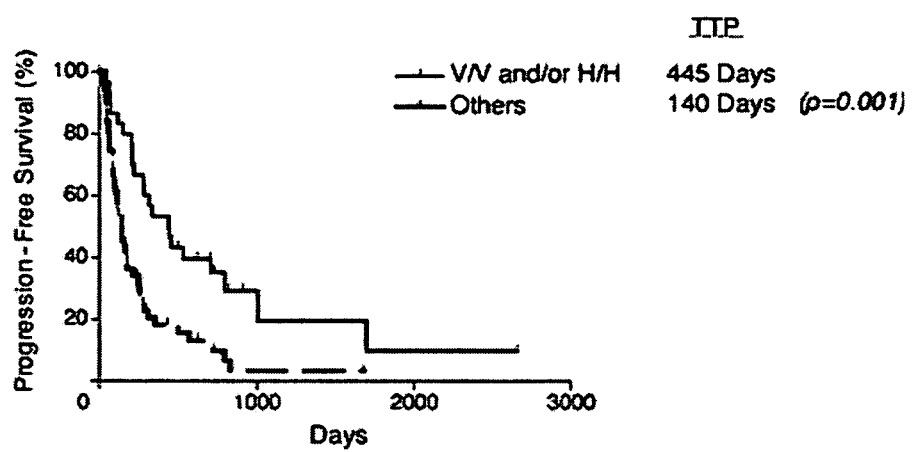
FIG. 4. Progression-free survival (PFS) by immunoglobulin G fragment C receptor IIIa (FcγRIIIa) 158 valine (V)/phenylalanine (F) and FcγRIIa 131 histidine (H)/arginine (R) polymorphisms. PFS curves were plotted by FcγRIIIa 158 V/F and FcγRIIa 131H/R genotype. Others represent patients without either FcγRIIIa 158 VN or FcγRIIa 131H/H genotype. TTP, median time to progression.

The possibility of an association between FcγRIIIa and FcγRIIa genotypes that might explain the correlation of the two with response rate was examined. As shown in Table 5, FIG. 9, there was no significant difference in the fraction of 158 V/V or F carrier in three 131H/R genotypes. The combination of FcγRIIa 158 V/V and/or FcγRIIa 131H/H was then analyzed, and their relationship to rituximab response. As shown in Table 6, FIG. 10, patients with 158 V/V and/or 131H/H (total of 30 patients) had a significantly higher response rate than patients without either genotype at all four time points (83% v 54%, P=0.009 at 1 to 3 months; 80% v 34%, P=0.0001 at 6 months; 69% v 26%, P=0.0003 at 9 months; 59% v 18%, P=0.0004 at 12 months). The PFS estimate of patients with 158V/V and/or 131H/H was also significantly longer (P=0.001), with TTP of 445 and 140 days for the two groups, respectively (FIG. 4). By logistic regression analysis, FcγRIIIa 158 V/V genotype emerged as the only predictive factor for response at 1 to 3 months, whereas both the FcγRIIIa 158 V/V genotype and FcγRIIa 131H/H genotype were identified as independent predictive factors for response at 6, 9, and 12 months (Table 7, FIG. 11).

III. Discussion

In this study, the observation of Cartron et al, supra, that 158 V/V genotype is associated with higher response rate to rituximab treatment was confirmed. However, there were some differences between the present and prior studies. First, the response rate in the patient group of the present study was lower than that in the previous report, especially at 12 months after treatment. This observation is consistent with previous observations of a lower response rate when rituximab is used as second-line treatment. In addition, the patients of the present study probably had higher tumor burden because 53% of them had bulky (≥5 cm) disease compared with the previous study in patients with nonbulky disease. Second, although F carriers (V/F and F/F) showed a significantly lower response rate, the response rate in patients with 158 F/F was slightly higher than that in patients with 158 V/F. The biologic explanation of this phenomenon is unclear, given that patients with 158 V/F would be expected to have an intermediate response rate. Third, consistent with the previous report, we detected a difference between 158 V/V and F carrier. However, one interesting observation in this study is that the difference became more pronounced after longer times from the treatment. The antibody is known to persist for up to 6 months, and its effect may be cumulative.

The most unexpected result came from the analysis of FcγRIIa polymorphism. The Allele of 131H/H binds to human IgG2 better than that of 131 R/R. However, no significant difference in the affinity of these two allelic forms for human IgG1 has been noted. (Parren P W, Warmerdam P A, Boeije L C, et al: On the interaction of IgG subclasses with the low affinity Fc-gamma-RIIa (CD32) on human monocytes, neutrophils, and platelets: Analysis of a functional polymorphism to human IgG2. J Clin Invest 90:1537-1546, 1992). Therefore, it was unexpected to find a higher rituximab response rate associated with 131H/H genotype (Table 4, FIG. 8). Similar to the FcγRIIIa 158 V/F polymorphism, a gene dosage effect of the 131H allele was not observed. Instead, the response rate in patients with 131H/R was similar to that of 131 R/R at 6,9, and 12 months. The biologic explanation of this observation is not clear. The association between FcγRIIa 131H/H and higher response rate was not a result of a linkage disequilibrium of FcγRIIa 158 V/F polymorphism (Table 5, FIG. 9). There is a random distribution of combinations of variant genotypes of FcγRIIa and FcγRIIIa in the normal population. (Lehrnbecher T, Foster C B, Zhu S, et al: Variant genotypes of the low-affinity Fc-gamma receptor in two control populations and a review of low-affinity Fc-gamma receptor polymorphisms in control and disease populations. Blood 94:4220-4232, 1999)

The FcγRIIa 131H/R polymorphism is an independent predictive factor for clinical response: In the subgroup of patients with 158 F carrier, FcγRIIa 131H/H genotype was associated with higher response rate at 6, 9, and 12 months (H/H=76% v R carrier=34%, P=0.004 at 6 months; H/H=65% v R carrier=26%, P=0.007 at 9 months; H/H=47% v R carrier=18%, P=0.026 at 12 months). Furthermore, all three patients with both 158 V/V and 131H/H genotypes had long-lasting remissions (Table 6, FIG. 10). Patients with 158 V/V and/or 131H/H genotypes showed a higher response rate and a longer remission than did patients without either of these two genotypes (Table 6, FIG. 10). Lastly, the logistic regression analysis showed that the 158 V/V and 131H/H were independent predictive factors for response at 6, 9, and 12 months. The report of Cartron et al, supra, also analyzed the FcγRIIa 131H/R polymorphism and concluded that the FcγRIIa polymorphism did not influence the clinical response. However, it is important to point out that Cartron et al analyzed a smaller group of patients (N=45) and scored the clinical responses only at 1 and 12 months. In this study, the most prominent differences were observed at 6 and 9 months (Table 4, FIG. 8).

It is evident that subject invention provides a convenient and effective way of determining whether a patient will be responsive to antineoplastic, e.g., antibody, therapy. The subject methods will provide a number of benefits, including avoidance of delays in alternative treatments, elimination of exposure to adverse effects of therapeutic antibodies and reduction of unnecessary expense. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a human subject suffering from non-Hodgkin's lymphoma (NHL) comprising:
    (a) obtaining a nucleic acid sample from the subject;
    (b) detecting in said nucleic acid the presence of a FcγRIIa H/H genotype;
    (c) correlating the presence of said FcγRIIa H/H genotype with an increased likelihood of responsiveness to IgG anti-CD20 antibody treatment; and
    (d) treating said subject with administration of an IgG anti-CD20 antibody.

2. The method of claim 1, wherein the method further comprises identifying a FcγRIIIa 158 polymorphism result for the subject, wherein the FcγRIIIa polymorphism result is a 158 V/V, 158 V/F, or 158 F/F genotype.

3. The method of claim 2, wherein identification of the FcγRIIIa 158 V/V genotype indicates an increased likelihood of responsiveness to said IgG anti-CD20 antibody as compared to a 158 F carrier genotype.

4. The method of claim 1, wherein said NHL is follicular lymphoma.

5. The method of claim 1, wherein said IgG anti-CD20 antibody is a monoclonal antibody.

6. The method of claim 5, wherein said monoclonal antibody is rituximab.

7. The method of claim 1, wherein the correlating comprises comparing the detected FcγRIIa H/H genotype to a FcγRIIa genotype control.

8. The method of claim 7, wherein said FcγRIIa genotype control is a therapy responsive control.

9. The method of claim 8, wherein the therapy responsive FcγRIIa genotype control is the FcγRIIa 131 H/H genotype.

10. The method of claim 1, further comprising determining for said subject a probability of progression-free survival.

11. The method of claim 1, wherein said IgG anti-CD20 antibody promotes antibody-dependent cell cytotoxicity (ADCC).

12. The method of claim 1, wherein said detecting comprises amplifying a portion of the FcγRIIa gene sequence comprising nucleic acids encoding amino acid residue 131 from the nucleic acid sample.

* * * * *